United States Patent
Hausmanns et al.

(10) Patent No.: US 9,386,783 B2
(45) Date of Patent: *Jul. 12, 2016

(54) CONFECTIONERY PRODUCTS AND PROCESS FOR OBTAINING THEM

(75) Inventors: Stephan Hausmanns, Wiesbaden (DE); Tillmann Dörr, Hohen-Sülzen (DE); Jörg Kowalczyk, Eisenberg-Steinborn (DE); Rainer Kliss, Reinheim (DE); Tilo Poth, Weinheim (DE); Badr Nfissi, Düsseldorf (DE); André Schirlitz, Neuss (DE)

(73) Assignees: SÜDZUCKER AKTIENGESELLSCHAFT MANNHEIM/OCHSENFURT (DE); HENKEL AG & CO. KGAA (DE)

(*) Notice: Subject to any disclaimer, the term of this patent is extended or adjusted under 35 U.S.C. 154(b) by 496 days.

This patent is subject to a terminal disclaimer.

(21) Appl. No.: 11/831,674

(22) Filed: Jul. 31, 2007

(65) Prior Publication Data

US 2009/0035355 A1 Feb. 5, 2009

(51) Int. Cl.

| A61K 9/00 | (2006.01) |
|---|---|
| A23G 1/54 | (2006.01) |
| A23G 3/02 | (2006.01) |
| A23G 3/36 | (2006.01) |
| A23G 4/06 | (2006.01) |
| A61K 33/06 | (2006.01) |
| A61P 43/00 | (2006.01) |
| A23G 1/32 | (2006.01) |
| A23G 3/54 | (2006.01) |
| A23G 4/20 | (2006.01) |

(52) U.S. Cl.
CPC *A23G 1/325* (2013.01); *A23G 1/54* (2013.01); *A23G 3/362* (2013.01); *A23G 3/54* (2013.01); *A23G 4/064* (2013.01); *A23G 4/20* (2013.01)

(58) Field of Classification Search
CPC ........... A23G 1/325; A23G 1/54; A23G 4/20; A23G 3/54; A23G 4/064; A23G 3/362
See application file for complete search history.

(56) References Cited

U.S. PATENT DOCUMENTS

| 5,645,853 | A | 7/1997 | Winston et al. |
| 6,849,286 | B1 | 2/2005 | Bayerköhler et al. |
| 2001/0016208 | A1* | 8/2001 | Valentine et al. ............. 424/465 |
| 2005/0008582 | A1 | 1/2005 | Du-Thumm et al. |
| 2006/0034975 | A1* | 2/2006 | Schechner et al. ................ 426/3 |
| 2008/0160091 | A1 | 7/2008 | Kropf et al. |
| 2008/0175904 | A1* | 7/2008 | Mathiesen et al. ............ 424/464 |
| 2008/0299194 | A1 | 12/2008 | Kolter et al. |

FOREIGN PATENT DOCUMENTS

| CA | 2230682 | 3/1997 |
| CA | 2 356 115 A1 | 6/2000 |
| DE | 195 32 395 | 4/1996 |
| DE | 195 32 396 A1 | 3/1997 |
| DE | 196 39 342 | 7/1998 |
| DE | 198 58 662 A1 | 6/2000 |
| DE | 199 30 335 A1 | 1/2001 |
| DE | 10 2004 050 954 A1 | 4/2006 |
| JP | 10-511104 | 10/1998 |
| JP | 2002-529496 | 9/2002 |
| JP | 2003-509384 | 3/2003 |
| WO | WO 97/06774 | 2/1997 |
| WO | WO 00/28973 | 5/2000 |
| WO | WO 2004/028262 | 4/2004 |
| WO | WO 2006/042582 A1 | 4/2006 |
| WO | WO 2007/071581 A2 | 6/2007 |
| WO | WO 2009/015791 A2 | 2/2009 |

OTHER PUBLICATIONS

Shen P., et. al., Remineralization of Enamel Subsurface Lesions by Sugar-free Chewing Gum Containing Casein Phosphopeptide-Amorphous Calcium Phosphate, J Dent Res. 80 (12): 2066-2070, 2001.*
Jacob, Michael, An introduction to continuous fluidized-bed agglomeration and spary granulation, Pwder and Bulk Engineering vol. 18, No. 4, Apr. 2004, CSC publishing Inc, pp. 1-9.*
CDC, Recommendations for Using Fluoride to Prevent and control Dental Caries in the United States, Aug. 17, 2001, pp. 1-44.*
Merriam-Webster: Agglomerate. Retrieved on Sep. 2, 2014. Retrieved from the internet <URL: http://www.merriam-webster.com/dictionary/agglomerate>.*
Japanese Office Action dated Sep. 13, 2011 of corresponding Japanese Patent Application No. 2010-518532.
Office Action dated Sep. 4, 2012 in corresponding Japanese Patent Application No. 2010-518532 (English translation).
Larry L. Hench and June Wilson, Editors, "An Introduction to Bioceramics," World Scientific, Advanced Series in Ceramics—vol. 1, relevant Chapter 3 and list of contents, New Jersey, 1993.
International Search Report dated Apr. 21, 2009 in parallel International Publication No. WO 2009/015791 A3 (International Application No. PCT/EP2008/005926)(4 total pages).
European Communication dated Oct. 12, 2015 in parallel European Patent Application No. EP 08 784 899.0 (7 total pages).

* cited by examiner

*Primary Examiner* — Anoop Singh
*Assistant Examiner* — Doan Phan
(74) *Attorney, Agent, or Firm* — Ostrolenk Faber LLP

(57) ABSTRACT

Agglomerates comprising calcium-hydrocolloid-composite materials and at least one sugar alcohol, as well of methods for preparing the agglomerates and various applications thereof.

49 Claims, 6 Drawing Sheets

CONFECTIONERY PRODUCTS AND PROCESS FOR OBTAINING THEM

TECHNICAL FIELD

The present invention relates to agglomerates comprising a calcium hydrocolloid-composite material and at least one sugar alcohol, as well as to confectionery products comprising the agglomerate and to processes for obtaining the agglomerates.

BACKGROUND OF THE INVENTION

Due to the ever-increasing demand by customers for confectionery products, which do not only appeal because of their taste but also because of functional benefits, more and more innovative confectioneries are developed. Among them are in particular are those which provide some health effects to the consumer, such as sugar-free confectionery products, which are acariogenic and suitable for consumers suffering from diabetes. Sugar-free confectionery products of this type are disclosed for instance in DE 195 32 395 C2 and DE 196 39 342 C2. Numerous additional references describe comestibles, in particular chewing gums and candies, which are prepared with the use of sugarless constituents, such as sugar alcohols and which, due to the absence of sucrose, provide some health effects.

However, while these products do not harm the health, in particular the health of teeth, it would be advantageous to provide confectionery which actually promotes the health of the consumer. To this end WO 2004/028262 describes the use of chewing gums which are coated and wherein in at least one of the coating layers a slightly water soluble calcium salt or a mixture of such a calcium salt with a further component is contained. Such a chewing gum is said to promote remineralisation of the tooth material, i.e., it compensates for the loss of minerals in the tooth material. It is furthermore said that the material allows a so-called neomineralisation process, which leads to a formation of biomimetic material.

SUMMARY OF THE INVENTION

The neomineralisation process provided by such chewing gums as those described above is, however, efficient only to a limited extent. It is therefore one object of the present invention to provide products which are of a confectionery nature but which additionally provide a beneficial health effect, in particular an improved remineralisaton and neomineralisation effect on the teeth.

The present invention solves the problem identified in the prior art by providing an agglomerate comprising a calcium-hydrocolloid-composite material and at least one sugar-alcohol. The problem is further dealt with by the provision of processes for obtaining the agglomerate and through the formation of confectionery products comprising the agglomerate, or else made from it.

DETAILED DESCRIPTION

Surprisingly, it has been found that confectionery products comprising the advantageous agglomerates of the present invention do not only provide considerably health benefits, both inter alia by pre-serving and promoting tooth health, but that they also show a very favourable organoleptic and sensoric profile. The products comprising the agglomerates of the present invention surprisingly display an extremely homogenous distribution of their constituents, namely the sugar alcohol component, in particular of the calcium salt component and the hydrocolloid-component, which improves the smoothness of the surface, the texture of the overall product and the acceptance by the consumer. Most advantageously, the calcium salt, in particular the calcium-hydrocolloid-composite material is very homogenously and finely distributed in the agglomerate and in particular in products containing the agglomerate or which are made from it, which in turn allows a high density and homogenous application of the composite material to the consumer, in particular his teeth and other oral organs. Thus, the present invention leads to a better dispersion of the calcium components and enables an improved, in particular more constant and faster release of its calcium components. Evidently, this is due to the formation of the presently developed agglomerates, which, due to the intimate and non-separable combination of the at least one sugar alcohol and the calcium hydrocolloid-composite material, provides a specific structural contribution to the products.

Thus, preferably, the identity of the present agglomerates can be recognised by light and scanning electron microscopy, in particular by Energy dispersive X-ray spectroscopy (EDX) with simultaneous site specific mapping of the elements, in particular calcium and phosphorous.

In a particularly preferred embodiment, the existence of the present agglomerates in the products of the present invention can be recognised by light and scanning electron microscopy, in particular by Energy dispersive X-ray spectroscopy (EDX) on embedded samples of the confectionery products.

By addition of the present agglomerates comprising the, preferably slightly water-soluble, calcium salt in form of its composites, new layers of a biometric material can form on the tooth. This material is chemically and structurally very similar to the natural hard tooth tissue. Therefore it not only compensates the mineral content of calcium and phosphate deficient regions (lesions) with their crystal structure still in place (common remineralisation of teeth), but also forms new material, which adheres to the tooth and is dentine-like in its nanostructure (neomineralization of teeth). Remineralising in the present context is the redeposition of ions in tooth material, that is the filling in of ion deficient lesions within the existing hard tissue such as enamel and dentine. This new formation of biometric material is termed hereinafter neomineralisation. In the context of the present invention the term mineralisation comprises not only remineralisation but also neomineralisation.

In the context of the present invention composite materials are composites which comprise a calcium salt, preferably a slightly water-soluble calcium salt, and at least one other component, namely the hydrocolloid-material, which composite material appears microscopically heterogeneous but macroscopically homogenous.

Agglomerates of at least one sugar alcohol with the composites of, preferably slightly water-soluble, calcium salts with hydrocolloid components, preferably protein components, in addition to remineralisation of the tooth, are also able to reduce the extent of relatively large damage in tooth dentine and/or tooth enamel by the formation of completely new crystals.

In the natural formation of calcified tissue, for example tooth material, a protein matrix causes the ordered deposition of hydroxyapatite in the tooth or bone, which protein matrix in the case of dentine principally consists of collagen and also other proteins. With the present agglomerates comprising the composites of the, preferably slightly soluble, calcium salt and hydrocolloids, the neomineralisation proceeds in a similar manner to biomineralisation and this leads to a particularly beneficial effect on tooth health.

In the context of the present invention, an agglomerate is a product obtained by an agglomeration process. An agglomeration process is a process of physically combining at least two different substances in a manner that they cannot be divided any more by physical separation steps, such as centrifugation, sieving, sedimentation etc.

In a particularly preferred embodiment of the present invention, agglomerates are small crystals of a milled sugar alcohol combined with a calcium-hydrocolloid-composite material. Such an agglomerate provides a superior, in particular homogenous and uniform disintegration and dissolution profile, in particular with regard to its calcium component. The calcium-hydrocolloid-composite material functions in this regard as a binder of the sugar alcohol particles.

In a preferred embodiment of the present invention, an agglomerate is a product, which has been obtained by the use of a fluidised bed agglomeration process, in particular using a fluidised bed agglomerator. A fluidised bed agglomeration process is characterised by distributing both of the substances to be agglomerated in a fluidising bed, in particular in a stream of a liquid or a gas, in particular air, which fluidises the substances and subjects them to conditions to produce an agglomerate. In a particularly preferred embodiment, the agglomerate of the present invention is prepared by spraying the calcium-hydrocolloid-composite material in the form of an aqueous dispersion and the at least one sugar alcohol in dry and powdered form in a fluidising air stream, whereby both substances can be sprayed simultaneously or one after the other, i.e. first the at least one sugar alcohol and then the aqueous dispersion or first the aqueous dispersion and then the at least one sugar alcohol.

In a preferred embodiment of the present invention, the sugar-alcohol is selected from the group consisting of isomalt, isomalt GS, 1,1-GPM (1-O-α-D-glucopyranosyl-D-mannitol), 1,6-GPS (6-O-α-D-glucopyranosyl-D-sorbitol), 1,1-GPS (1-O-α-D-glucopyranosyl-D-sorbitol), a mixture of 1,1-GPS, 1,1-GPM and 1,6-GPS, xylitol, lactitol, mannitol, maltitol syrup, maltitol, sorbitol and erythritol.

In a particularly preferred embodiment of the present invention, the sugar alcohol used is in the form of particles having a diameter of less than 100 µm, preferably less than 50 µm, in particular wherein 90% of said particles have a diameter of less than 100 µm, preferably less than 50 µm.

In the context of the present invention isomalt GS is a mixture of 1,6-GPS and 1,1-GPM in a ratio from 71 to 79% 1,6-GPS and 21 to 29% 1,1-GPM, preferably 75% 1,6-GPS to 25% 1,1-GPM. Isomalt is a mixture of 43 to 57% 1,6-GPS and 43 to 57% 1,1-GPM, preferably a 1:1 mixture (values given in weight-% on dry matter).

In a further preferred embodiment of the present invention, the sugar alcohol used is a milled isomalt, in particular a milled isomalt, wherein the milled isomalt particles have a diameter less that 100 µm (PF), preferably less than 50 µm (PA).

In a preferred embodiment of the present invention, the agglomerate comprises the at least one sugar-alcohol, in particular isomalt or isomalt GS, in form of particles, wherein 90% of said particles have a diameter of less than 100 µm, preferably less than 50 µm.

In a particularly preferred embodiment, the used sugar alcohol, in particular isomalt or isomalt GS is used in form of particles, wherein all or at least 90% of the particles have a diameter of less than 100 µm, preferably less than 50 µm. In a preferred embodiment, these particles lead to a particularly preferred, uniform and homogenous distribution of the calcium component, that means the calcium salts, throughout the complete agglomerate, including its centre and surface. Thus, in this preferred embodiment, the use of the isomalt or isomalt GS-particles having a diameter of less than 100 µm, preferably less than 50 µm, lead to a three-dimensional, homogenous and uniform distribution, without the formation of local clusters or higher concentrations of the calcium component, for instance on the surface of the agglomerate.

In a preferred embodiment of the present invention, the sugar-alcohol particles are distributed homogenously in the agglomerate.

In a preferred embodiment of the present invention, the calcium-hydrocolloid-composite material comprises a calcium salt and a hydrocolloid-component.

In a preferred embodiment of the present invention the agglomerate comprises the calcium salt in form of particles of the calcium salt having a diameter less than 1000 nm, preferably wherein at least 90% of said particles have a diameter of less than 1000 nm.

In a furthermore preferred embodiment, the calcium salt used according to the present invention is used in form of crystallites or in form of particles comprising a multitude of crystallites or particles, the particles having a mean particle diameter of less than 1000 nm, preferably less than 300 nm, and wherein the particles preferably are rod- or platelet-shaped, and in particular in a platelet-like form.

In a further preferred embodiment, a single crystallite of the calcium salt according to the present invention has a width from 2 to 50 nm and a length from 10 to 150 nm, preferably a width of 2 to 15 nm and a length of 10 to 50 nm, preferably a width of 3 to 11 nm and a length of 15 to 25 nm.

In a further preferred embodiment, the calcium salt used according to the present invention has a mean particle diameter of less than 1000, preferably less than 300 nm.

In a further preferred embodiment, the particles of the calcium salt used have a platelet-like form and a length of 10 to 150 nm and a width of 5 to 150 nm.

In a further preferred embodiment, the particles of the calcium salt have a relation of length to width from 1 to 4, preferably 1 to 3, most preferably 1 to 2.

In a further preferred embodiment of the present invention, the particles of the calcium salts have a size of $0.1 \times 10$ to $15 \, m^2$ to $90 \times 10$ to $15 \, m^2$, preferably $0.5 \times 10$ to $15 \, m^2$ to $50 \times 10$ to $15 \, m^2$, preferably $1.0 \times 10$ to $15 \, m^2$ to $30 \times 10$ to $15 \, m^2$, in particular $1.5 \times 10$ to $15 \, m^2$ to $15 \times 10$ to $15 \, m^2$.

Particle size as described herein is measured by Scanning Electron Microscopy (SEM) and Transmission Electron Microscopy (TEM) or other optical or screening techniques, for example using a Coulter counter.

In a preferred embodiment of the present invention, the particles of the calcium salt have a diameter of 5 to 300 nm, preferably wherein at least 90% of the particles have a diameter of 5 to 300 nm.

In a preferred embodiment of the present invention the calcium salt is a slightly water-soluble calcium salt, preferably in form of rod- and platelet-shaped crystals.

Slightly water-soluble calcium salt refers to salts which, at 20° C., are soluble in water at less than 0.1 by weight (1 g/l).

According to a preferred embodiment, the, preferably slightly water-soluble, calcium salt has a particle size or particle fineness less than 1000 nm. In the context of the present invention, particle fineness is the diameter of the particles in the direction of their greatest length. The mean particle size fineness relates to a volume-averaged value.

According to a preferred embodiment, the calcium salt, preferably the slightly water-soluble calcium salt has a particle size or particle fineness of 5 to 300 nm, in particular 5 to 100 nm. An advantage of these particularly low particle sizes or particle finenesses is that the primary particles exhibit particularly effective remineralisation of the teeth and, moreover, have the ability to form new, neomineralised layers of material very similar to the hard tooth tissue.

According to a particularly preferred embodiment, the calcium salts have an elongated shape, in particular rod- or platelet-like shape. This has the particular advantage that they are very similar to the shape of the biological apatites, for example bone apatites or dentine apatites, and therefore have a particularly good capability for remineralisation and neomineralisation.

In a preferred embodiment of the present invention, the particles of the calcium salt have a diameter of 20 to 70 nm, preferably 20 to 30 nm, preferably wherein at least 90% of said particles have a diameter of 20 to 70 nm, preferably 20 to 30 nm.

Preferred calcium salts for the present invention are calcium hydroxyphosphate ($Ca_5[OH(PO_4)_3]$) or hydroxyapatite, calcium fluorophosphates ($Ca_5[F(PO_4)_3]$) or fluorapatite, fluorine-doped hydroxyapatite of the composition ($Ca_5(PO_4)_3(OH,F)$ and calcium fluoride ($CaF_2$) or fluorite or fluorspar, and also other calcium phosphates such as di-, tri- or tetracalcium phosphate ($Ca_2P_2O_7$, $Ca_3(PO_4)_2$, $Ca_4P_2O_9$), oxyapatite ($Ca_{10}(PO_4)_6O$) or non-stoichiometric hydroxyapatite ($Ca_{5-1/2(x+y)}(PO_4)_{3x}(HPO_4)_x(OH)_{1-y}$). Cabonate-containing non-stoichiometric apatite also preferred for example $Ca_{5-1/2(x+y+z)}(PO_4)_{3-x-z}(HPO_4)_x(CO_3)_z(OH)_{1-y}$, calcium hydrogen phosphate, for example $CaH(PO_4).2\,H_2O$ and octacalcium phosphate, for example $Ca_8H_2(PO_4)_6.5\,H_2O$.

In a preferred embodiment of the present invention, the calcium salt is selected from the group consisting of apatite, hydroxyapatite, fluoroapatite, fluorine-doped hydroxyapatite, carbonate-containing nonstoichiometric apatite, carbonate apatite and carbonated fluoroapatite.

Most preferred calcium-hydrocolloid composite materials of the present invention are particularly those which comprise finely divided slightly soluble calcium salts, preferably hydroxyapatite nanoparticles, which have a clearly discernible crystalline morphology, the particle fineness of which is therefore in the range from 5 to 300 nm and finely divided proteins, protein hydrolysates or derivatives thereof form a spatial structure in such a manner that the finely divided calcium salts lie on the protein structure and quasi spatially reproduce these. Composite materials which consist of such preferably suitable nanoparticulate calcium salts and protein components lead to particularly good mineralisation of the teeth on consumption of products containing sugar alcohol agglomerates therefrom.

Slightly water-soluble calcium salts can add to the protein chains particularly readily in rod form. This leads to a markedly improved cohesion of the composite material. Minerals which are suitable in particular here are primary particles having a particle fineness of 5 to 300 nm, and preferably 5 to 100 nm, since these particularly small crystallites are very similar to the shape of biological apatites and, because if the small size, can also add still better to the protein chains. These composites lead as a result to a particularly effective mineralisation of teeth.

A preferred calcium salt of the present invention is a finely divided slightly water-soluble calcium salt which is selected from hydroxyapatite, carbonate-containing non-stoichiometric apatite, fluoroapatite, fluorine-doped hydroxyapatite and mixtures thereof.

In a preferred embodiment of the present invention, the calcium salt is homogenously distributed in the agglomerate.

In a preferred embodiment of the present invention, the hydrocolloid component is a protein component.

According to the present invention, hydrocolloid materials, in particular protein components are adsorbed to the surface of the calcium salts, as a result of which a composite material of the hydrocolloid material, preferably protein component, and the calcium salt, preferably slightly water-soluble calcium salt, is formed. In the present composites the primary particles of the calcium salts are associated to the backbone of the hydrocolloid, in particular protein, component. In particular, by means of the adsorbed colloid, preferably protein, component coagulation and agglomeration of the calcium salts is also prevented and the crystal growth is retarded. In the case of mineralisation of a tooth, and in particular in the case of neomineralisation, it is of great advantage if no uncontrolled crystal growth takes place which could only form a loose crystal structure. By means of the protein backbone, the crystal growth can proceed in controlled manner. Thus, a particularly tight and solid crystal structure is formed.

The protein component preferably present in the composite is selected in particular from proteins, protein breakdown products and derivatives of proteins or protein breakdown products.

Preferred protein components are all proteins independent of their origin, for instance animal proteins, plant proteins or proteins from microorganisms. Preferred animal proteins are, for example, collagen, fibroin, elastin, keratin and albumin. Preferred plant proteins are, for example, wheat products and wheat germ products (gluten), rice protein, soybean protein, oat protein, pea protein, almond protein and potato protein. Single-cell protein, for example yeast protein or bacterial proteins, are also suitable.

Protein breakdown products are those products, which are obtainable by hydrolytic, oxidative or reductive breakdown of water-insoluble proteins to give oligopeptide and polypeptide structures having lower molecular weight and having an improved water solubility.

The hydrolytic breakdown of water-insoluble proteins is the most important breakdown method; it can proceed under the catalytic influence of acids, alkalis or enzymes. Those which are preferably suitable are, especially, those protein breakdown products which are not broken down further than is required to achieve the water solubility.

The less broken-down protein hydrolysates comprise for example gelatine which is preferred in the context of the present invention, and which can have molar masses in the range from 15 000 to 400 000 D. Gelatine is a polypeptide which is principally produced by hydrolysing collagen under acidic or alkaline conditions. Particular preference is given to gelatine produced under acidic or strongly acidic conditions or under enzyme action.

In the context of the present invention, derivates of proteins and protein breakdown products are chemically modified proteins or protein hydrolysates which are obtainable, for example, by acylation of free amino groups, by addition of ethylene oxide or propylene oxide and hydroxyl, amino or carboxyl groups or by alkylation of hydroxyl groups of the protein or protein breakdown product or of a hydroxyalkyl derivative thereof, for example with epoxypropyltrimethylammonium chloride or 3-chloro-2-hydroxypropyltrimethylammonium chloride.

In a particular preferred embodiment, the hydrocolloid component is a protein component being selected from the group consisting of gelatine, hydrolysates thereof and casein and hydrolysates thereof.

The amount of the hydrocolloid, in particular protein, components in the calcium-hydrocolloid composite material is preferably from 0.1 to 50% by weight, but preferably from 1.0 to 45% by weight, in particular 20 to 40% by weight, based on the weight of the overall calcium-hydrocolloid-composite material. In a preferred embodiment, the amount of the hydrocolloid, in particular protein, component in the calcium-hydrocolloid-composite material is from 35 to 45%, in particular 40% based on the dry weight of the calcium-hydrocolloid-composite material.

In a further preferred embodiment, the amount of the calcium salt in the calcium-hydrocolloid-composite material is from 50 to 99.9 weight-%, preferably from 55 to 99 weight-%, preferably from 60 to 80 weight-%, most preferably from 55 to 65 and in particular 60 weight-% of the dry weight of the calcium-hydrocolloid-composite material.

In a particularly preferred embodiment, the calcium-hydrocolloid-composite material comprises 0.1 to 50 weight-%, preferably 1.0 to 45 weight-%, most preferably 20 to 40 weight-% hydrocolloid-component and 50 to 99.9 weight-%, preferably 55 to 99 weight-% and preferably 60 to 80 weight-% calcium salt.

In a further preferred embodiment, the calcium-hydrocolloid-composite material may, in addition to the above-identified two components may comprise further components, i.e. so called composite additives for instance calcium phosphate in amorphous form, preferably in an amount of 0.1 to 40 weight-% (based on the dry weight of the calcium-hydrocolloid-composite material).

In a preferred embodiment, the amount of the calcium-hydrocolloid-composite material in the agglomerate of the present invention is from 0.05 to 5.0%, preferably from 0.1 to 2.0%, most preferably from 0.5 to 1.5%, in particular from 0.2 to 2.0 weight-% based on the dry weight of the agglomerate.

In a particularly preferred embodiment, the amount of the at least one sugar alcohol in the agglomerate of the present invention is from 95.0 to 99.95%, preferably from 98.0 to 99.9%, preferably from 98.5 to 99.5, in particular from 98.0 to 99.8% based on the dry weight of the agglomerate.

In a further preferred embodiment of the present invention the agglomerate comprises 0.05 to 5.0 weight-%, preferably 0.1 to 2.0 weight-%, preferably 0.5 to 1.5 weight-%, preferably 0.2 to 2.0 weight-% of the calcium-hydrocolloid-composite material and 95.0 to 99.95 weight-%, preferably 98.0 to 99.9 weight-%, preferably 98.5 to 99.5 weight-%, preferably 98.0 to 99.8 weight-% of the at least one sugar alcohol. Preferably, such an agglomerate may optionally also comprise 0.1 to 40 weight-% (based on dry weight of the agglomerate) agglomerate additives, as explained below.

In a further preferred embodiment it is foreseen that the agglomerate may, in addition to both components above, that means in addition to the calcium-hydrocolloid-composite material and the at least one sugar alcohol, may comprise further components, i.e. so called agglomerate additives, such as calcium phosphate in amorphous form, preferably in an amount from 0.1 to 40 weight-% (based on dry weight of the agglomerate).

The water content of the agglomerates is preferably from 1.5 to 6 weight-%, preferably from 2 to 5.5 weight-%, based on overall weight of the agglomerates.

In a particularly preferred embodiment, the agglomerates of the pre-sent invention have an ash content (grav., 800° C.) from preferably 0.1 to 1 weight-% (based on dry weight), preferably from 0.1 to 0.7 weight-%.

In a further preferred embodiment of the present invention, the agglomerates of the present invention have an overall nitrogen content (KJ) from preferably 0.3 to 1 weight-‰, preferably from 0.4 to 0.9 weight-‰ (based on dry weight).

In a preferred embodiment of the present invention, the agglomerate has a diameter of 63 to 1000 µm, preferably 100 to 800 µm, preferably at least 90% of the agglomerates have a diameter of 63 to 1000 µm, preferably 100 to 800 µm.

In a preferred embodiment of the present invention, the agglomerate has a diameter of 100 to 500 µm, preferably at least 90% of the agglomerates have a diameter of 100 to 500 µm.

In a preferred embodiment of the present invention, at least 60%, at least 70%, at least 80%, preferably at least 90%, in particular at least 95%, preferably at least 99.9% of the agglomerate (based on dry weight of agglomerate) is the calcium-hydrocolloid composite material and the at least one sugar-alcohol.

In a preferred embodiment of the present invention, the agglomerates of the present invention have a bulk density in $g/cm^3$ from preferably 0.30 to 0.70, preferably from 0.40 to 0.55.

In a further preferred embodiment of the present invention, the agglomerates of the present invention have a tamped density in $g/cm^3$ from preferably 0.40 to 0.70, preferably from 0.50 to 0.65.

In a further preferred embodiment of the present invention, the agglomerates of the present invention have an angle of repose from preferably 32 to 38°, preferably from 34° to 37°.

In a furthermore preferred embodiment of the present invention, the agglomerates of the present invention have a flowability (6 mm)/flow time in s/100 g from 38 to 49 s/100 g, preferably from 39 to 49 s/100 g.

In a further preferred embodiment, the agglomerates of the present invention have a d' (mm) from preferably 0.20 to 0.45, preferably from 0.30 to 0.45.

In a preferred embodiment of the present invention, the calcium salt, the calcium-hydrocolloid composite material or both are or is coated by one or more surface modification agents. Preferably, the calcium salt, in particular the finely divided calcium salt, is coated with at least one surface modification agent.

By this means, for example, the production of composite materials can be facilitated in those cases in which the nanoparticulate calcium salts are dispersed with difficulty. The surface-modification agent is adsorbed to the surface of the nanoparticles and changes in such a manner that the dispersibility of the calcium salt increases and the agglomeration of the nanoparticles is prevented.

Furthermore, a surface modification can influence the structure of the composite materials and also the loading of further components with the nanoparticulate calcium salt. In this manner, when the composite materials are used in mineralisation processes, it is possible to affect the course rate of the mineralisation process.

Surface modification agents are, in the context of the present invention, substances which adhere physically to the surface of the finely divided particles but do not chemically react with them, The individual molecules of the surface-modification agents which are adsorbed or bound to the surface are essentially free from intermolar bonds. Surface-modification agents are taken to mean, in particular, dispersants. Dispersants are known to those skilled in the art under the terms surfactants and protective colloids. Suitable surfactants or polymeric protective colloids are disclosed in DE 198 58 662 A1.

In a preferred embodiment of the present invention, the present invention relates to a confectionery product or a coating thereof, which comprises the present agglomerates. The products of the present invention provide a superior, homogenous and uniform release of its calcium components, which in turn allows to close dentinal tubules of the consumers teeth in an improved manner. Accordingly, the products of the present invention are particularly useful for the treatment of pain-sensitive teeth. In particular, the calcium components are homogenously distributed throughout the confectionery product, for instance a hard caramel, or if applied in a coating, throughout the coating. In a preferred embodiment the present invention relates to sugar free confectionery products or sugar free coating of confectionery products comprising the present agglomerates.

In a particularly preferred embodiment of the present invention there is also provided a confectionery product, preferably a sugar-free product, which is made from the agglomerate of the present invention, preferably made substantially from such agglomerates. In the context of the present invention a confectionery product made from an agglomerate of the present invention refers to those products, for whose production the agglomerates are used, in particular wherein 0.1 to 100% of the educts are the agglomerates, preferably 1 to 100%, most preferably 2%, 3%, 4%, 5%, 6%, 7%, 8%, 9%, 10%, 20%, 30%, 40%, 50%, 60%, 70%, 80%, 90% or 95% to 100% of the products (based on the amount of dry substance of which the product is comprised).

In a particularly preferred embodiment the confectionery product comprises the agglomerate in an amount from 10%, 20%, 30%, 40%, 50%, 60%, 70%, 80% or preferably 90% to 100% (based on dry weight of the product).

In a further preferred embodiment the confectionery product comprises the agglomerate in an amount from 10% to 50%, preferably 10% to 40%, preferably 20% to 35% by weight (based on dry weight of the product).

In a further preferred embodiment, the confectionery product comprises the agglomerate in an amount from 70% to 99.8%, preferably 80% to 99.6%, most preferably 90% to 99.5% by weight (based on dry weight of the product).

In a further preferred embodiment, it is evident that depending upon to the specific nature of the confectionery product comprising the agglomerates of the present invention, further product additives may be present in the confectionery product or its coating.

Depending upon the nature of the confectionery product, it comprises 0.05 to 60 weight-%, preferably 0.1 to 60 weight-%, preferably 1 to 50 weight-%, most preferably 1 to 40 weight-% of such product additives. Such product additives are food and sweetening ingredients, such as intense sweeteners, gum bases, plastifiers, lubricant, emulsifier, protein components, dairy ingredients, milk components, fat and fat substitutes, vegetable fat, vitamins, minerals, pharmaceutically active ingredients, preservatives, aroma, flavourings, such as peppermint, menthol, fruit, strawberry flavour, colours, $TiO_2$, edible acids, such as citric acid, and dietary fibres.

Particularly preferred is that the confectionery product or, if the product is a coated product, in particular the coating thereof, comprises in addition to the agglomerates of the present invention, casein, a component of casein, a phosphoprotein, a phosphopeptide or a salt thereof, wherein said phosphoprotein or phosphopeptide comprises phosphoserine, phosphothreonine, phosphotyrosine, phosphohistidine or phospholysine. Preferably, the confectionery products or coatings thereof comprise casein phosphopeptides (CPP), in particular phosphoserin, preferably together with di- or trivalent metals such as CaCPP, FeCPP, ZnCPP, calcium phosphate CPP or calcium fluoride CPP.

In a particularly preferred embodiment the confectionery product of the present invention, in particular a chewing gum, hard or soft caramel, or if the product is coated, preferably the coating thereof comprises casein phosphopeptide-amorphous calcium phosphate (CPP-ACP) as a further substance to remineralise enamel subsurface lesions in teeth.

In a further preferred embodiment, the present confectionery products or if coated, preferably the coating thereof, in particular chewing gums or hard caramels, comprise CPP-ACP and citric acid in addition to the agglomerates of the present invention.

In a further preferred embodiment the present invention relates to confectionery products, or in the case where the confectionery products are coated, preferably the coating thereof, comprising the agglomerates of the present invention and a two-phase-system comprising as one phase at least one water-soluble calcium-compound and as another phase comprising at least one water-soluble inorganic phosphate and, optionally at least one water-soluble fluorine compound, wherein, in a further preferred embodiment the water-soluble calcium salt may be calcium chloride or calcium nitrate.

In a further preferred embodiment, the present invention relates to confectionery products, or in the case that the confectionery products are coated, preferably the coating thereof, comprising the agglomerates of the present invention and a complex comprising arginine together with calcium, carbonate and bicarbonate (CaviStat®/SensiStat®).

In a further preferred embodiment of the present invention, there is provided a confectionery product or, in case the confectionery product is a coated product, preferably the coating thereof, which comprises in addition to the agglomerates of the present invention, a nerve-desensitising agent selected from the group consisting of a potassium salt, a strontium salt, a combination of zinc or strontium ions and mixtures thereof. Preferably, the salts may be associated with a controlled dissolution composition, comprising at least one water-swellable or water soluble polymer.

In a further preferred embodiment of the present invention, there are provided confectionery products, or in the case that the confectionery products are coated product, preferably coatings thereof, which comprise in addition to the agglomerates of the present invention, a modified enzyme comprising an enzyme and at least one polyanionic domain, for instance polyglutamic acid, polyaspartic acid or a polycarboxylic acid, wherein the enzyme comprises or is covalently attached to each of said polyanionic domain.

In a further preferred embodiment of the present invention, there is provided a confectionery product, or in case the confectionery product is a coated product, preferably a coating thereof, which comprises in addition to the agglomerates of the present invention a water-soluble calcium-phosphate salt, or a monolithic combination of calcium and phosphate salts in a first carrier and additionally an alkaline material and a fluoride ion source in a second carrier.

In a further preferred embodiment, the present invention provides confectionery products of the present invention, or if coated, preferably the coating thereof, in particular chewing gums, or soft or hard caramels, which in addition to the agglomerates of the present invention comprise tetracalcium phosphate/dicalcium phosphate.

In a further preferred embodiment of the present invention, there is provided a confectionery product, or in case the confectionery product is a coated product, preferably a coating thereof, which comprises in addition to the agglomerates of the present invention bioactive glass particles, in particular bioactive glass particles having a particle size of ≤25 µm, ≤15 µm, preferably ≤10 µm. Bioactive glass for use in the present invention is described for example in "An introduction to Bioceramics", Hench and Wilson, Editors, World Scientific, New Jersey, (1993).

In a preferred embodiment of the present invention, the confectionery products include bioactive glass particles with a composition as follows: from 40 to 90% by weight of silicon dioxide ($SiO_2$), from 4 to 50% by weight calcium oxide (CaO), from 1 to 15% by weight phosphorous oxide ($P_2O_5$) and from 0 to 35% by weight of sodium oxide ($Na_2O$). Preferably, the bioactive glass includes from 40 to 60% by weight of silicon dioxide ($SiO_2$), from 10 to 30% by weight calcium oxide (CaO), from 2 to 8% by weight phosphorous oxide ($P_2O_5$) and from 10 to 30% by weight sodium oxide ($Na_2O$). The oxides can be present as solid solutions or mixed oxides, or as a mixture of oxides.

In a furthermore preferred embodiment, $Al_2O_3$, $B_2O_3$, $CaF_2$, MgO or $K_2O$ may in addition be included in the glass particles. The preferred range for $CaF_2$ is from 0 to 25% by weight. The preferred range for $B_2O_3$ is from 0 to 10% by weight. The preferred range for $Al_2O_3$ is from about 0 to 5% by weight. The preferred range for $K_2O$ is from 0 to 10% by weight. The preferred range for MgO is from 0 to 5% by weight.

In a particularly preferred embodiment the confectionery products of the present invention comprise as product additives intense sweeteners being selected from cyclamate, saccharin, aspartame, glycyrrhicine, neohesperidine-dihydrochalcone, steveoside, in particular steveosides with a high content of rebaudioside A, thaumatin, monellin, acesulfame, alitame, sucralose and mixtures thereof.

In a preferred embodiment of the present invention the product is selected from the group consisting of chewing gums, a chocolate product, a toffee, a marsh mallow, a nougat, a pastille, a lozenge, a fudge, a fondant, jelly, gum, tablets, hard candies and soft candies.

In the context of the present invention a hard candy and a soft candy is also called a hard caramel and a soft caramel.

In a particularly preferred embodiment, the present invention provides confectionery products, which have superior organoleptic and sensoric properties, which constantly and uniformly release its calcium salt content and simultaneously provide beneficial effects on the consumers' health. Most likely due to the specific structure of the agglomerate comprising the agglomerated combination of the calcium-hydrocolloid-composite material and the at least one sugar alcohol, it is possible to produce confectionery products, which display an extremely homogenous distribution of its ingredients, in particular the calcium salt and the hydrocolloid material, which in turn leads to favourable characteristics.

In a preferred embodiment of the present invention a hard candy is provided comprising the agglomerates of the present invention or being made from them, in particular agglomerates comprising a calcium-hydrocolloid-composite material and isomalt. In a furthermore preferred embodiment, the present invention provides a hard candy comprising agglomerates of the present invention or being made from them comprising a calcium-hydrocolloid-composite material and isomalt GS. Preferably, in both of these embodiments, the hydrocolloid component is gelatine and the calcium salt is apatite. Hard candies of the present invention, in particular those in which the amount of the calcium-hydrocolloid-composite material and the at least one sugar alcohol is at least 60%, at least 70%, preferably at least 80%, in particular at least 90%, most preferably at least 95% (weight-% on dry matter of hard caramel) display a very smooth surface, a homogenous distribution of the gelatine and in particular the calcium components and are judged by consumers as having an excellent organoleptic and sensoric profile. Said hard candies can be prepared by mixing the agglomerates of the present invention with the other ingredients of the hard candy to be obtained and heating them, for example by cooking or extruding, to obtain a hard candy which subsequently is formed and cooled.

In a preferred embodiment of the present invention the confectionery product is a coated product. In a preferred embodiment, the coated product is a coated jelly, a coated gum, a coated chocolate product, a coated toffee, a coated chewing gum, a coated soft caramel or a coated tablet.

In a preferred embodiment of the present invention the agglomerate is contained in the coating and preferably is solely contained therein.

In a particularly preferred embodiment of the present invention a coated product is provided, in particular a coated product comprising a soft caramel, a tablet or chewing gum core, wherein the coating comprises the agglomerates of the present invention or is made from them.

In a particularly preferred embodiment, the coating of such a coated soft caramel comprises the agglomerates of the present invention or is made from them in an amount of at least 60%, at least 70%, at least 80%, preferably at least 90% in a particularly preferred embodiment to at least 95% (based on the dry weight of the coating).

In a particularly preferred embodiment, the present invention provides coated chewing gums, wherein the coating comprises the agglomerate according to the present invention or is made from them. In a particularly preferred embodiment the coating of such a chewing gum comprises the agglomerate in an amount of at least 60%, at least 70%, at least 80%, preferably at least 90%, particularly preferred at least 95% of the overall coating (based on dry weight of the coating).

Such a coating provides a superior organoleptic and sensoric coating combining beneficial health and consumer-attractive features. Both the calcium salt and the hydrocolloid component are evenly and homogenously distributed in the coating. Preferably, the at least one sugar alcohol used in the agglomerate for such a soft caramel or chewing gum is isomalt or, most preferred isomalt GS.

In a preferred embodiment of the present invention, a coated chewing gum or a soft caramel is provided wherein the coating comprises at least 2 to 100 coating layers.

In a further preferred embodiment, the chewing gum or soft caramel core is coated by at least one hard coating step.

In a further preferred embodiment of the present invention, the hard coating step comprises applying a solution or suspension, comprising at least the agglomerates of the present invention to the chewing gum or soft caramel cores and drying the applied solution or suspension. In a particularly preferred embodiment the drying of the applied solution or suspension is done by passing air over the coated cores and therefore drying them by air, in particular an air stream, preferably at a temperature from 20 to 80° C.

In a further preferred embodiment, the invention foresees the above-identified chewing gum or soft caramel, wherein the chewing gum comprises a core being coated by at least one soft coating step. In a particularly preferred embodiment, the soft coating step comprises applying a solution or suspension, which comprises coating ingredients, preferably the agglomerate of the present invention, to the chewing gum or soft caramel cores and dusting the applied solution or suspension with a dry and powdered substance, in particular a sugar alcohol or agglomerate of the present invention. Thus, in one preferred embodiment, the agglomerates may be added to the core in the coating medium or in another preferred embodiment they may be added in the dusting step. In another preferred embodiment they may be added in both.

In a further preferred embodiment of the present invention, the coated products are coated in a combined soft and hard coating process, wherein the drying of the coating solution or suspension is achieved both by drying with air, particularly air with a temperature from 20 to 80° C., and by dusting the applied solution or suspension with a dried and powdered substance, wherein in a preferred embodiment the amount of said dry and powdered substance is from 20 to 75% of the overall coating ingredients.

In a particularly preferred embodiment of the present invention, the solution or suspension used in the soft or hard coating process comprises the total amount of the agglomerates or a part thereof.

In a further preferred embodiment, the dry and powdered sugar alcohol and the dry and powdered agglomerate of the present invention used for the dusting step is the total amount of the sugar alcohol or the agglomerate or a part thereof.

In a further preferred embodiment part of the coating ingredients, in particular part of the at least one sugar alcohol and part of the agglomerate of the present invention, is present in the coating solution or suspension and another part is used for dusting in form of a dry and powdered form.

In a further preferred embodiment, the hard coating or soft coating steps are repeated several times, preferably 2 to 120 times to obtain a corresponding number of coating layers.

Furthermore, the present invention provides chewing gums comprising as both sweetening and bulking agent the agglomerates of the present invention, in particular in an amount of at least 20 weight-%, at least 30 weight-%, at least 40 weight-% and preferably at least 50 weight-% up to preferably 60, preferably 70 weight-% (based on dry weight of the overall chewing gum). Preferably, the at least one sugar alcohol used in the agglomerate is isomalt or isomalt GS. Such chewing gums have the advantage that the ingredients, in particular the calcium salt and the hydrocolloid-component are evenly and homogenously distributed in the chewing gum mass and provide an improved organoleptic and sensoric behaviour.

In a further preferred embodiment, the present invention relates to compressed products, in particular tablets, comprising the agglomerates of the present invention or made from it. Preferably, such tablets comprise the agglomerate in an amount of at least 70%, at least 80%, preferably at least 90%, particularly preferred at least 95% based on the dry weight of the compressed products. These products display an improved organoleptic and sensoric behaviour and display a very smooth surface.

Calcium-hydrocolloid-composite materials for use in the present invention can preferably be produced by precipitation from aqueous solutions of water-soluble calcium salts with aqueous solutions of water-soluble phosphate and/or fluoride salts in the presence of hydrocolloid, in particular protein, components. Various methods are described in DE 199 30 335.

The present composite materials in which the primary particles of the calcium salts are surface modified can be produced by similar precipitation methods as described above, but with the precipitation of the nanoparticulate calcium salts or of the composite materials taking place in the presence of one or more surface-modification agents.

In a preferred embodiment of the present invention, the process for the preparation of an agglomerate comprising a calcium-hydrocolloid-composite material and at least one sugar-alcohol comprises a) providing a calcium-hydrocolloid-composite material and at least one sugar-alcohol, b) distributing the at least one sugar-alcohol and the calcium-hydrocolloid-composite material in a fluidising bed, in particular in a stream of gas or liquid, under conditions suitable to agglomerate them. In a preferred embodiment of the present invention the agglomeration in step b) is performed as a fluidised bed agglomeration, in particular in a fluidised bed agglomerator or in a continuously operated installation.

In a particularly preferred embodiment, the fluidising stream of gas or liquid is a fluidising stream of air.

In a preferred embodiment of the present invention, the calcium-hydrocolloid-composite material is provided and distributed in the fluidising bed in form of a dispersion, in particular an aqueous dispersion, preferably by spraying it in the fluidising gas or liquid, in particular into the air stream. Preferably said spraying is done under pressure. Preferably, the aqueous dispersion is of a gel-like structure of high viscosity which has been heated to above 40° C., preferably 50° C.

Preferably, said dispersion is a homogenous dispersion of the calcium-hydrocolloid-composite material in water.

In a preferred embodiment of the present invention the at least one sugar-alcohol is provided and distributed in the fluidising bed in solid form, preferably by spraying the at least one sugar-alcohol in the fluidising gas or liquid, in particular air stream. Preferably, the spraying is done under pressure.

In a particularly preferred embodiment, conditions suitable to agglomerate refer to conditions, wherein the calcium-hydrocolloid-composite material and the at least one sugar alcohol are brought into contact, in particular close or intimate physical contact with each other. In a particularly preferred embodiment, the conditions suitable to agglomerate also refer to conditions under agitation, preferably under increased pressure, and preferably under increased temperatures.

In a preferred embodiment of the present invention, it is foreseen that both the calcium-hydrocolloid-composite material and the at least one sugar alcohol are sprayed simultaneously in the fluidising bed, in particular the stream of air or liquid.

In a furthermore preferred embodiment it is foreseen that first the at least one sugar alcohol is placed or distributed in the fluidising bed, in particular is sprayed into it, in particular in dry and powdered from into the fluidising stream of gas or liquid, and thereafter the aqueous dispersion of the calcium-hydrocolloid-composite material is sprayed thereon.

In a further embodiment of the present invention, first the aqueous dispersion of the calcium-hydrocolloid-composite material is placed or distributed in the fluidising bed, in particular is sprayed, in particular into the fluidising stream of gas or liquid, and thereafter the at least one sugar alcohol is sprayed in dry and powdered form thereon.

In a particularly preferred embodiment of the present invention, the calcium-hydrocolloid-composite material is added to the sugar alcohol in the fluidising bed, in particular the gas or liquid, in particular air stream, preferably under pressure, by spraying, in particular through a nozzle.

In a further preferred embodiment, the spraying pressure for the calcium-hydrocolloid-composite material is preferably from 2.0 bar to 4.0 bar.

In a particularly preferred embodiment, the process for the preparation of an agglomerate is a continuously operated process. In another embodiment, the process of the present invention is a discontinuously operated process.

In a particularly preferred embodiment, the aqueous dispersion of the calcium-hydrocolloid-composite material comprises 8% to 20%, preferably 10% to 15%, most preferably 12% of the calcium-hydrocolloid-composite material and 80% to 92%, preferably 85% to 90%, most preferably 88% of water (based on total weight of aqueous calcium hydrocolloid-composite material dispersion).

Preferably, the temperature of the aqueous calcium-hydrocolloid-composite material dispersion for use in the agglomeration process is from 55 to 60° C.

In a particularly preferred embodiment of the present invention, the at least one sugar alcohol used in the process of the present invention is isomalt GS, in particular GS-PA (GS-PA refers to isomalt GS, wherein 90% of the particles are smaller than 50 µm). Said sugar alcohol is particularly useful for the production of coatings of coated products.

In a further preferred embodiment, the at least one sugar alcohol, preferably used is isomalt ST, preferably isomalt ST-PA (ST-PA refers to isomalt ST, wherein 90% of the particles are smaller than 50 µm). Said sugar alcohol is preferably useful for the production of hard candies.

In a preferred embodiment of the present invention the proportion of the aqueous calcium hydrocolloid-composite material dispersion to the at least one sugar alcohol, preferably in solid form, is from 5% to 30%, preferably 50% to 25%, preferably 5% to 20% and preferably 10% to 25% aqueous dispersion to 70% to 95%, preferably 75% to 95% and preferably 80% to 95%, preferably 75% to 90% (each based on weight of overall agglomeration dispersion) of the at least one sugar alcohol.

In a particularly preferred embodiment, the agglomeration, i.e. contacting time in step b) is from 45 min to 90 min, preferably 60 min.

In a particularly preferred embodiment, the agglomerate obtained in step b) is subjected to a milling process.

In a preferred embodiment of the present invention the agglomerate obtained in step b) is subjected to a size-fractionation, for instance in a tumble classifier or oscillating screening machine.

In a particularly preferred embodiment the agglomerates are size-fractionated so as to obtain agglomerates comprising 90% of the particles greater than 90 µm.

In a particularly preferred embodiment the agglomerates of the present invention have a particle size distribution, wherein 90% of the agglomerates particles are greater than 90 µm. In a preferred embodiment, the agglomerates have a specific surface of 6.0 to 7.2 m$^2$/g, in particular of 6.2 m$^2$/g. In a preferred embodiment, the agglomerates have a porosity of 45 to 55%, particularly 45%.

Preferably, the size fractionation is done in a screening machine, in particular a sieving machine. Preferably, the size of the obtained agglomerates is from 0.1 mm to 1.0 mm, most preferably from 0.1 mm to 0.5 mm.

In a preferred embodiment of the present invention the agglomerate obtained in step b) is dried after the agglomeration, preferably with a stream of air, so as to obtain an essentially dry agglomerate, preferably a dry agglomerate.

In a preferred embodiment of the present invention the agglomerate is dried after the size-fractionation.

In a particularly preferred embodiment, the drying time of the agglomerates is from 10 to 30 min, preferably 20 min. In a furthermore preferred embodiment, the drying temperature of the inlet drying air is from 65 to 100° C., preferably 80° C. In a furthermore preferred embodiment the temperature of the agglomerates is from 45° C. to 70° C., preferably from 50° C. to 60° C.

The production of the agglomerates of the present invention can also be achieved by wet agglomeration and subsequent drying in a fluidising bed.

The production of the agglomerates of the present invention can also be achieved by spray drying of a suspension comprising the sugar alcohol and the calcium-hydrocolloid-composite material.

In a preferred embodiment, the present invention also relates to agglomerates obtainable by any one of the above-identified processes, in particular to size fractionated and/or dried agglomerates.

The invention also relates to the use of agglomerates of the present invention and to methods of using them, according to which an effective amount of agglomerates or products containing the agglomerates of the present invention in an effective amount are prophylactically or therapeutically used for dental care, for dental repair, for caries prophylaxis, for caries treatment, to protect bone and teeth from damage, to repair bone and tooth defects or to form mineralised, remineralised or neomineralised bone or tooth structures, preferably tooth enamel and/or dentine, in particular in a human or animal body, preferably in organoleptically and sensorically improved confectionery products and in processes for their production.

The invention also relates to the use of agglomerates of the present invention and confectionery products containing them and to methods of using them according to which an effective amount of agglomerates or products containing an effective amount of the agglomerates of the present invention are prophylactically or therapeutically used in an animal or human body to fight pain-sensitive teeth, preferably in organoleptically and sensorically improved confectionery products and in processes for their production.

The invention also relates to the use of agglomerates of the present invention and confectionery products containing them and to methods of using them according to which an effective amount of agglomerates or products containing an effective amount of the agglomerates of the present invention are prophylactically or therapeutically used in an animal or human body to fight caries, preferably in organoleptically and sensorically improved confectionery products and in processes for their production.

The invention also relates to the use of agglomerates of the present invention and confectionery products containing them and to methods of using them according to which an effective amount of agglomerates or products containing an effective amount of the agglomerates of the present invention are prophylactically or therapeutically used in an animal or human body to remineralise tooth defects, preferably in organoleptically and sensorically improved confectionery products and in processes for their production.

Further preferred embodiments of the present invention are the subject-matter of the subclaims.

The present invention is furthermore illustrated by way of the following examples and the accompanying figures.

EXAMPLES

The following examples are provided only for the purpose of illustrating the invention and are not to be construed as limiting the invention in any manner.

Example 1

Production of Agglomerates

A) Production of an Apatite-Protein Complex

To produce the apatite-gelatin composite, 2000 ml of demineralised water are placed in a 4 l glass beaker thermostated to 25° C., in which 44.10 g (0.30 mol) of $CaCl_2 \cdot 2H_2O$ (Fisher Chemicals p.a.) are dissolved. Separately from this, 35 g of gelatin (type A, DGF-Stoess, Eberbach) are dissolved in 350 ml of demineralised water at about 50° C. Both solutions are combined and vigorously stirred with a propeller agitator. The pH is set to 7.0 using dilute aqueous base.

To this gelatin and calcium salt solution are added evenly by pumping, using an automated feed setup, with vigorous stirring in the course of 120 min, 300 ml of a 0.6 M $(NH_4)_2HPO_4$ solution which had previously been set to pH 7.0. The pH is held constant at pH 7.0 by controlled addition of dilute aqueous base. After completion of the addition, the solution is further stirred over 24 h. The dispersion is then charged into centrifuge tubes and the solids content separated from the solution by centrifugation. By extracting the residue five times by shaking into demineralization water and then renewed centrifugation, the salts are substantially extracted, so that chloride is no longer detectable. A apatite-gelatine-composite material is obtained.

B) Production of the Isomalt GS or Isomalt Agglomerate

Dry and powdered isomalt GS-PA or ST-PA is filled into a bed of a fluidizing bed agglomerator and the bed is fluidized.

Figure 1:
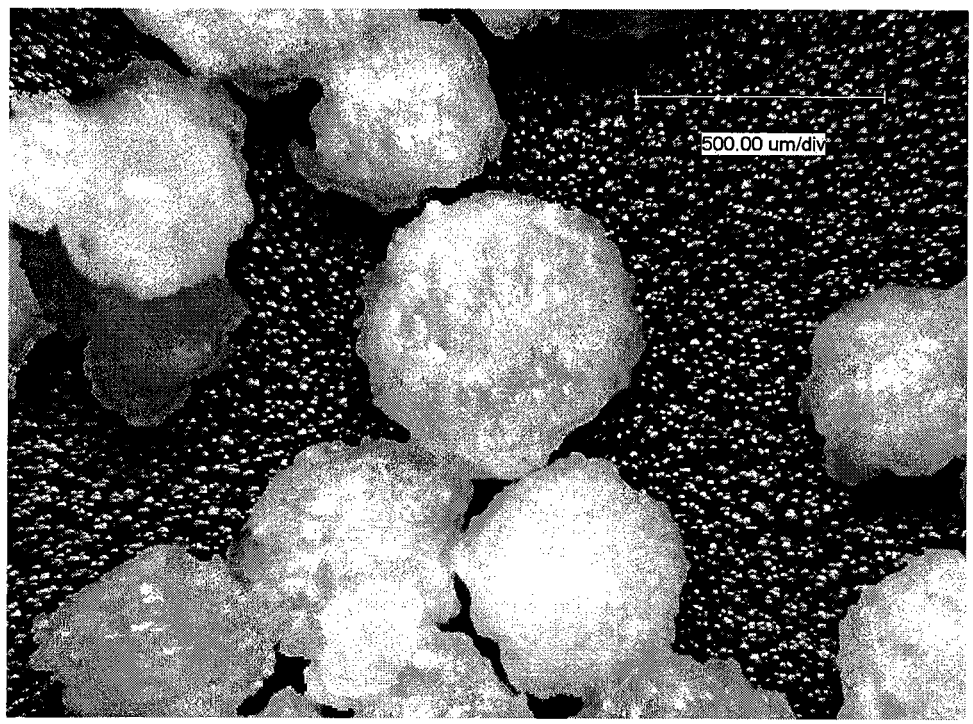
FIG. 1 shows an agglomerate comprising an apatite-gelatine-composite material (1%) and isomalt GS-F (90% of the particles with a size of 100-800 µm)
Figure 2:
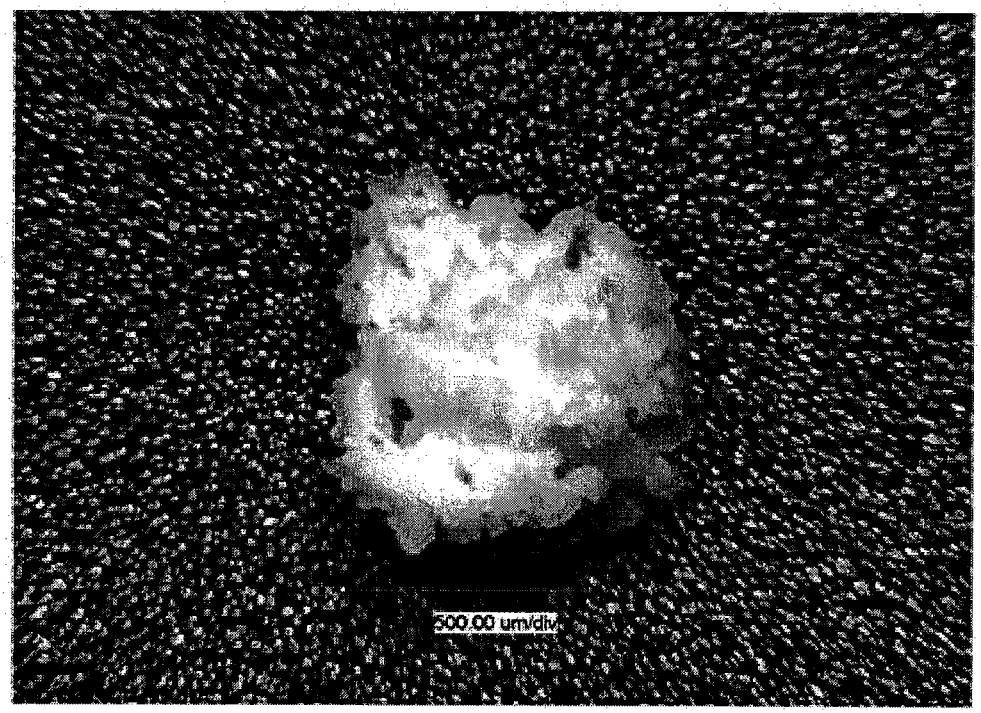
FIG. 2 shows an agglomerate comprising an apatite-gelatine-composite material (1%) and isomalt GS-PA.

The apatite-gelatine-composite material obtained in step A above is dispersed in water to obtain a dispersion comprising 88% water and 22% of the apatite-gelatine-composite. The dispersion has a temperature from 55 to 60° C. and is subjected to an intensive agitating process to obtain a quite solid gel-like structure with a homogenous distribution of its components. By a top/bottom spray system the composite material in aqueous dispersion is sprayed in a fluidizing air stream on the powdered isomalt GS-PA (for the preparation of coatings of chewing gums) or isomalt ST-PA (for the preparation of hard candies) sugar alcohol material. The proportion of the aqueous dispersion to the solid sugar alcohol is from 5 to 20% aqueous dispersion to 80 to 95% of the sugar alcohol. The spray rate for the dispersion is from 500 g/min to 5000 g/min, the sprayed amount is from 15 kg/h to 100 kg/h and the spray pressure from 2.5 bar to 4.0 bar. The agglomeration takes place for 60 minutes. Thereafter, the agglomerates are dried with a constant air flow at 80° C. inlet air temperature for 20 min, whereby the agglomerates have a temperature from 50 to 60° C. The agglomerates are then size-fractioned in a sieving machine (tumble classifier/oscillating screening machine) to obtain agglomerates from 0.1 to 0.5 mm. FIGS. 1 and 2 show agglomerates of the present invention. FIG. 1 is a microscopic photo of isomalt GS-F based agglomerates with a 1 weight-% calcium-hydrocolloid-composite material content and FIG. 2 of an isomalt-GS-PA based agglomerate comprising 1 weight-% of the calcium-hydrocolloid-composite material.

EDX analysis (compare example 6) of agglomerates containing either isomalt GS-PA (≤50 μm) or isomalt GS-F (100 bis 800 μm) (each with a 1% apatite-gelatin-composite material content) show for the isomalt GS-PA-based agglomerates a particularly uniform and homogenous three-dimensional distribution of the calcium component throughout the entire agglomerate, while for the GS-F-based agglomerate, a surface enriched calcium component distribution is to be observed.

Table 1 below lists physical and chemical parameters of an agglomerate prepared according to the above process.

TABLE 1

| Product | d05 [mm] | d95 [mm] | d' [mm] | n | water content (KF) [g/100 g] | bulk density [g/cm³] | Tamped density [g/cm³] | angle of repose [°] | flowability/flow time (6 mm) [s/100 g] |
|---|---|---|---|---|---|---|---|---|---|
| Agglomerated isomalt GS with apatite-gelatine-composite material | 0.67 | 0.08 | 0.37 | 2.0 | 2.8 | 0.49 | 0.59 | 34.7 | 46.9 |

Example 2

Coated Chewing Gum

TABLE 2

| Recipe of coating | Quantity |
|---|---|
| agglomerate of example 1 (comprising 1% apatite-gelatine-composite material and 99% isomalt GS) | 6500 g |
| Water | 3390 g |
| Aspartame | 5 g |
| acesulfam K | 5 g |
| Titandioxide | 100 g |
| Temperature of solution | 65° C. |
| Aroma | 50 g |
| polishing wax | 12 g |
| coating times | 163 min |
| Cores | 7.5 kg |

7.5 kg of conventional chewing gum cores have been coated in a conventional hard coating process at 65° C. for 163 minutes using the agglomerates of example 1 as main ingredient in the above-identified coating recipe. The coating of the chewing gum provided excellent organoleptic, optical and sensoric properties, in particular showed a particularly uniform distribution of the calcium-hydrocolloid-composite material.

The ash-content (800° C., grav.) (based on content in coating) of various samples of coated chewing gums in g/100 g was from 0.56 to 2.17. The overall nitrogen content (KJ) was in g/kg from 0.56 to 1.52.

Example 3

Peppermint Hard Candies

TABLE 3

|  | 0.25% apatite-gelatine-composite material in agglomerate,[x] sample 1 [g/100 g] | 0.5% apatite-gelatine-composite material in agglomerate,[x] sample 1 [g/100 g] | 0.25% apatite-gelatine-composite material in agglomerate,[x] sample 2 [g/100 g] | 0.5% apatite-gelatine-composite material in agglomerate,[x] sample 2 [g/100 g] |
|---|---|---|---|---|
| agglomerate of example 1 | 71.00 | 76.10 | 68.87 | 71.40 |
| water | 28.35 | 23.07 | 30.30 | 27.77 |
| acesulfam K | 0.05 | 0.05 | 0.05 | 0.05 |
| aspartam | 0.05 | 0.05 | 0.05 | 0.05 |
| peppermint flavouring (860.172 TD 1191 Firmenich) | 0.50 | 0.50 | 0.50 | 0.50 |
| Mastercote blue | 0.05 | 0.05 | 0.05 | 0.05 |

[x]The remainder of the substance of the agglomerate being isomalt ST

The ingredients are mixed and boiled to 155° C. to 160° C., cooled and formed to obtain a hard boiled candy.

The candies have a good transparency and lightness, a uniform distribution of its calcium components and a smooth surface. They show excellent shelf life behaviour.

Example 4

Sensoric Properties of Hard Caramels

Comparative Test

The sensoric evaluation of the hard caramels of the present invention showed in comparison to comparative hard candies as prepared below the following results:

TABLE 4

|  | Hard caramels from agglomerates of the present invention (0.5 weight-% content of composite material*) | Hard caramels from agglomerates of the present invention (1.0 weight-% content of composite material*) | Hard caramels from control mixture (0.5 weight-% content of composite material, no agglomerates*) | Hard caramels from control mixture (1.0 weight-% content of composite material, no agglomerates*) |
|---|---|---|---|---|
| Viscosity | 0.9 | 2.0 | 0.8 | 1.9 |
| sucking behaviour | 0.5 | 1.2 | 1.0 | 2.0 |
| Roughness | 0.0 | 0.25 | 1.25 | 2.0 |

[x]the remainder being isomalt ST

The comparative hard caramels were produced as follows in a cooking pot:

Heat isomalt and water to 170° C. in a cooking pot, cool,

Add separately an apatite-gelatine composite material and heat to 155° C.

Add other ingredients

Make hard caramels.

Example 5

Compressed Products/Tablets

TABLE 5

| Peppermint-tablets | Isomalt GS [g/100 g] |
|---|---|
| agglomerate of example 1 | 97.35 |
| Peppermint flavouring (29 00 43 Symrise) | 1.50 |
| menthol (163592 Symrise) | 0.50 |
| compritol, Fa. Gattefoss's | 0.50 |

TABLE 5-continued

| Peppermint-tablets | Isomalt GS [g/100 g] |
|---|---|
| acesulfam K | 0.05 |
| Aspartam | 0.10 |

TABLE 6

| Orange-tablets | Isomalt GS [g/100 g] |
|---|---|
| agglomerate of example 1 | 98.4 |
| Orange flavouring (648764 Symrise) | 0.50 |
| compritol, Fa. Gattefoss's | 0.50 |

TABLE 6-continued

| Orange-tablets | Isomalt GS [g/100 g] |
|---|---|
| citric acid | 0.50 |
| Aspartam | 0.10 |

The ingredients of the above-identified recipes were produced in plough shear mixers. The mixing time was at 150 U/min 4 minutes. Tablet were produced with a Fette rotary pelleting press 1200 (30 000 tablets/h). The tablets had a diameter of 12 mm, where round and had a weight of 500 mg.

Figure 3:
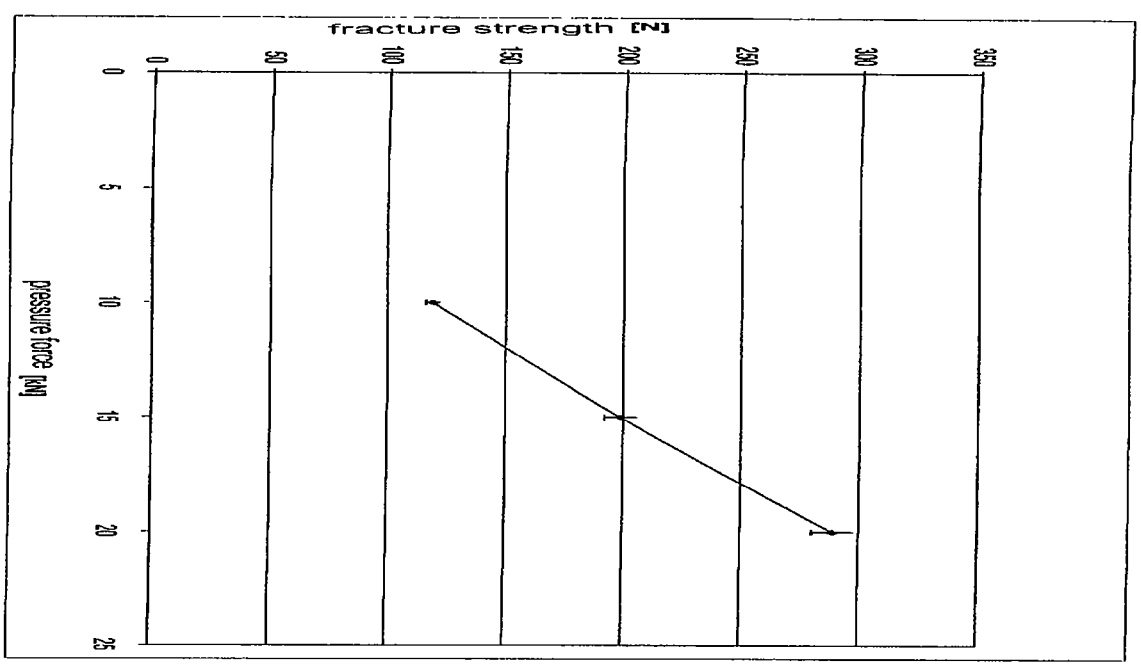
FIG. 3 shows the relation between fracture strength and pressure force in an isomalt-based tablet.

The same procedure was repeated with the recipe of table 6. FIG. 3 shows the fracture strength of the tablets in dependence upon the pressure force applied.

Example 6

Effects of Confectionery Products Comprising the Agglomerates on Dental Health

The confectionery products listed in table 12 comprising the agglomerates of example 1 have been prepared. The amount of the apatite-gelatine-composite material given below is calculated on the basis of the final confectionery product (for coated products based on coating alone) and not on the agglomerate containing the composite.

TABLE 7

| Product | Apatite-gelatine-composite material | Batch |
|---|---|---|
| hard caramel/menthol | 1% | MS 234/6 |
| hard caramel/menthol | 1% | MS 234/6 |
| hard caramel/menthol | 1% | MS 260/3 |
| hard caramel/menthol | 0.6% | MS 260/2 |
| hard caramel/menthol | 0.2% | MS 260/1 |
| hard caramel/menthol | placebo | MS 165/1 |
| hard caramel/menthol | 1% | MS 234/3 |
| hard caramel/menthol | 2% | MS 234/4 |
| coated chewing gums | 1% | H 2919 |
| coated chewing gums | 2% | H 2919 |
| coated chewing gums | 1% | Without |
| coated chewing gums | 2% | Without |
| tablets/menthol | 1% | MS 235/1 |
| tablets/menthol | 2% | MS 235/2 |
| tablets/menthol | 1% | MS 261/3 |
| tablets/menthol | 0.6% | MS 261/2 |
| tablets/menthol | 0.2% | MS 261/1 |
| tablets/menthol | 1% | MS 262/3 - granules |
| tablets/menthol | 0.6% | MS 262/2 - granules |
| tablets/menthol | 0.2% | MS 262/1 - granules |
| tablets/menthol | placebo | 2 RE 444 |
| soft caramel | 1% | MS 234/7 |

The SBF (simulated body fluid) solution is a solution that is equivalent to natural saliva with regard to the concentration relationships of the inorganic ions. This model fluid does not take into account the carbonate content of saliva or its organic components. The composition is summarized in the table below. With regard to the formation of hydroxy apatite, SBF, like natural saliva, is over-saturated in calcium and phosphate.

Composition of SBF

TABLE 8

| | Ion | | | | | |
|---|---|---|---|---|---|---|
| | $Ca^{2+}$ | $Na^+$ | $K^+$ | Phosphate | $Cl^-$ | pH |
| Concentration [mmol/l] | 1.8 | 14.0 | 21.0 | 4.7 | 30 | 6.5 |

In order to prepare an immersion solution, 6 g of the confectionery product given in table 12 and made from the agglomerates of example 1 was dissolved in 30 g of deionized water. Depending on the starting concentration of the agglomerates in the confectionery products, this resulted in a solution that contained between 12 and 60 mg of apatite-gelatine-composite material (equivalent to a concentration of 0.04 to 0.2 wt. %).

The solutions are easy to prepare from the hard-caramels. In the case of the coated chewing gums, the active ingredient-containing shell was first removed from the chewing mass by mechanical means. The compressed products of batch MS 235/x showed foam formation and flocculation, which was less pronounced in the case of the batches MS 261/x and 262/x.

TABLE 9

Concentration relationships of the apatite-gelatine-composite material in the immersion solutions employed

| Concentration of apatite-gelatine-composite material in the confectionery product* | Concentration of apatite-gelatine-composite material in the immersion solution | Quantity of apatite-gelatine-composite material in the immersion solution |
|---|---|---|
| 1% | 0.2% | 60 mg |
| 0.6% | 0.12% | 36 mg |
| 0.2% | 0.04% | 12 mg |
| 0 | 0 | 0 |

*for coated chewing gums: concentration in coating

Dentin discs with a size of approx. 0.8×0.8 cm were dissected from the roots of bovine teeth and then polished. The immersion experiments with the dentin discs aimed to mimic the chewing situation inside the mouth.

An automatic immersion apparatus was employed to carry out the immersion experiments. The apparatus is capable of immersing the dentin discs in the active ingredient solutions in an alternating fashion, whereby the immersion time can be set individually.

The following example reflects a typical immersion program:
1) immersion in active ingredient solution for 2 min
2) immersion in the SBF solution for 15 min (the SBF solution is changed every 2 hours)
3) repeat of the cycle for approx. 8 h After completion of the immersion program, the dentin discs are brushed for 30 seconds using a soft toothbrush and a mixture (water/glycerol). Then the discs are rinsed with SBF and dried on air.

ESEM (Environmental Scanning Electron Microscopy)

In a conventional scanning electron microscope, the sample to be tested is kept at a high vacuum of $10^{-5}$ Torr. The investigations were carried out using a Philips XL-30 Environmental Scanning Electron Microscope (ESEM) with EDAX-EDX. The measurements were carried out in low-vacuum mode at a water vapor pressure of approx. 0.7 Torr. The cathode voltage was 20 kV. For the measurements, the dentin discs were fixed to an aluminum carrier using conductive adhesive film. All discs were tested before and after treatment. The tests before treatment were done to identify suitable areas with exposed dentinal tubules. Suitable areas were marked by scratching with a scalpel. Representative images at 1,000×, 2,000×, and 4,000× magnification were stored. The discs were wetted with a Simulated Body Fluid (SBF) prior to the first treatment.

The investigation after the treatment also focused on the previously marked areas. The subsequent procedure was identical to that of the tests before.

EDX (Energy Dispersive X-Ray Analysis)

EDX is a classical procedure that is used for spatially-resolved analysis of the near-surface areas of solid bodies or for characterization of thin layers. The EDX procedure analyzes the X-ray emission spectrum caused by irradiating a sample with electrons (electron beam in a scanning electron microscope). Analysis of the spectral lines in the X-ray spectrum allows to identify the elemental composition of the sample and quantify it by means of the intensity. EDX is frequently combined with electron microscopy methods (REM or TEM). Scanning with a finely focused primary electron beam allows the elemental distribution on the sample surface to be imaged at high spatial resolution.

The test detects the deposition of dentine like material onto the specimens. The formation of the material can be well followed by the degree of occlusion of the dentinal tubules. The occlusion of dentinal tubules is a measure for the efficacy of the tested formulation in desensitizing teeth.

Results

Two placebo samples (hard-caramel and basic mass of compressed product) were tested for their neomineralizing effect. No closure of the dentin tubuli after immersion was evident. Storage of the dentin discs in SBF, i.e. without treatment with an immersion solution, also does not lead to closure of the dentin tubuli.

Hard-Caramels

The present example shows that the open dentinal tubules can be effectively closed by immersing the dentin discs in a solution that is made from hard-caramels comprising the agglomerates of the present invention. The layers thus generated appear very smooth in the electron microscope and cannot be removed from the tooth by mechanical means (brushing, treatment in an ultrasound bath). A closure is attained not only with candy with a apatite-gelatine-composite material content of 1 wt. % (dry weight of candy), but also at lower concentrations (0.6 and 0.2 wt. %). The layers produced at the lower active ingredient concentrations and equal immersion time are thinner which was evident in electron microscopy from a difference in the contrast ratio of the closed tubulus to the surrounding material.

The composition of the layers in terms of their quantitative ratio of calcium-phosphorus corresponds to that of natural hydroxy apatite.

Figure 4:
FIG. 4 shows dentine disks after treatment with immersion solutions made from hard caramels comprising agglomerates to a final content of 0.6 weight-% apatite-gelatine-composite material in the hard caramel.
Figure 5:
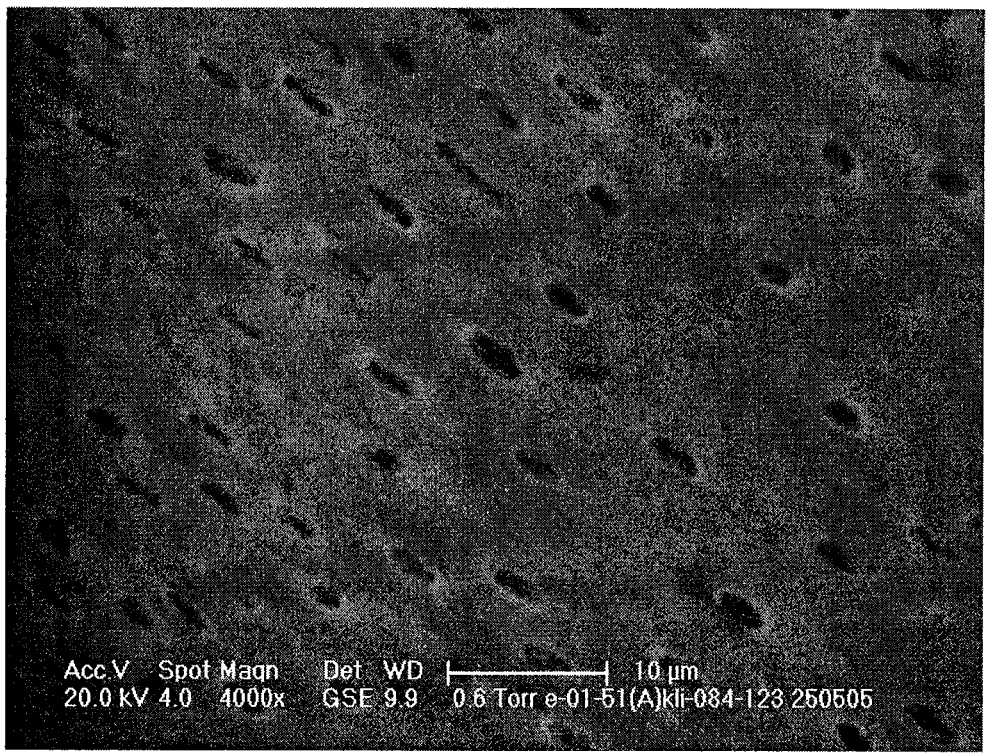
FIG. 5 shows dentine disks after treatment with immersion solutions made from hard caramels comprising agglomerates to a final concentration of 0.2 weight-% apatite-gelatine-composite material in the hard caramel.

FIGS. 4 and 5 show dentin discs after treatment with immersion solutions made from hard-caramels: 0.6 wt. % apatite-gelatine-composite material in a hard caramel (FIG. 4) vs. 0.2 wt. % apatite-gelatine-composite material in a hard caramel (FIG. 5).

Compressed Products

The use of the powdery and magnesium stearate-free compressed product raw mass of the second batch (MS 261/x) led to effective mineralization. As before, the growth of layers was observed at all apatite-gelatine concentrations employed in the investigation (0.2-1 wt. % apatite-gelatine-composite material in raw mass). The built-up material is smooth and mechanically resistant.

Figure 6:
FIGS. 6 to 8 show the treatment of dentin discs with immersion solutions made from compressed products comprising the agglomerates of example 1: untreated (FIG. 6); treatment with 1.0% apatite-gelatine-composite material-containing compressed product granulate (FIG. 7); treatment with 0.2% apatite-gelatine-composite material-containing compressed product granulate (FIG. 8)
Figure 7:
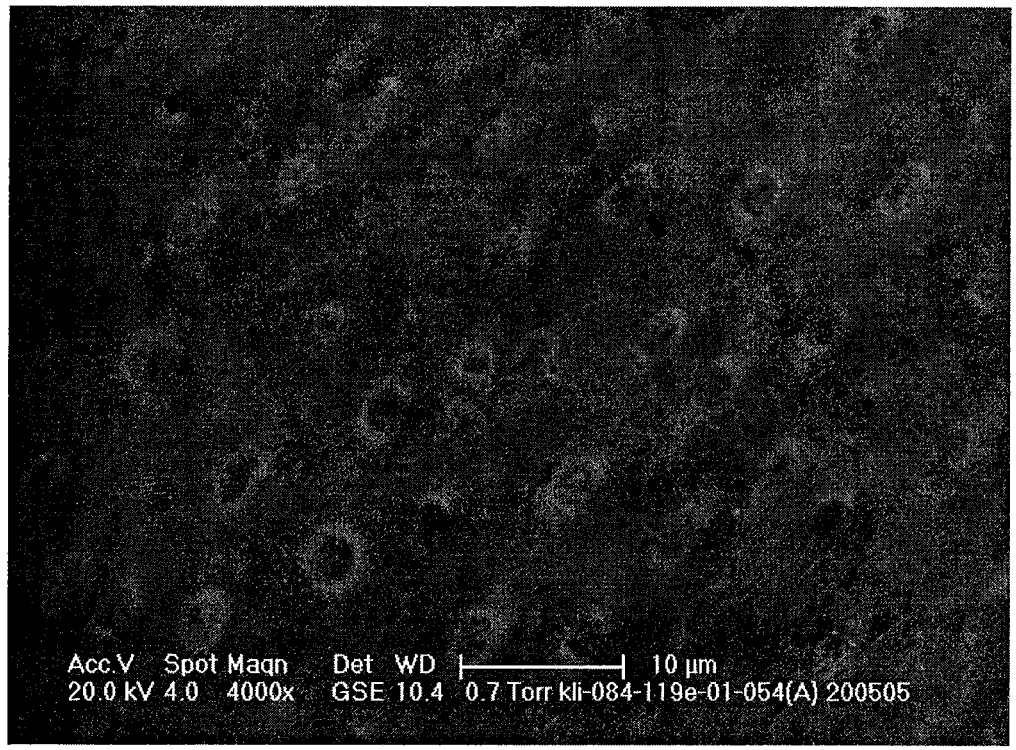
Figure 8:
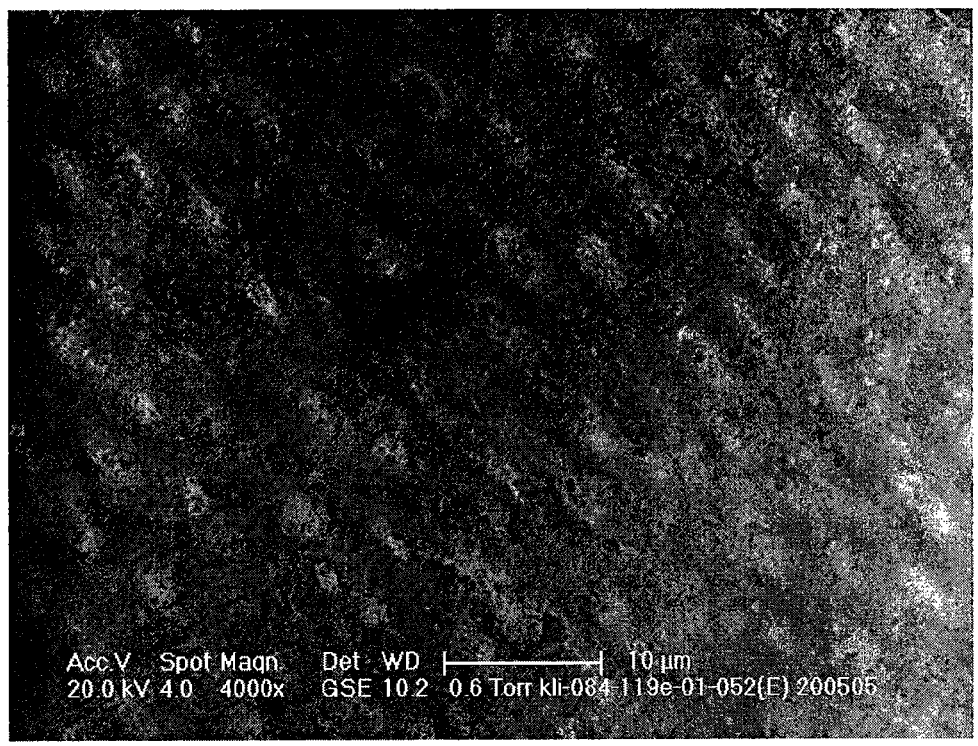

FIGS. 6 to 8 show the treatment of dentin discs with immersion solutions made from compressed products comprising the agglomerates of example 1: untreated (FIG. 6); treatment with 1.0% apatite-gelatine-composite material-containing compressed product granulate (FIG. 7); treatment with 0.2% apatite-gelatine-composite material-containing compressed product granulate (FIG. 8).

Coated Chewing Gums

The agglomerates containing the apatite-gelatine-composite material were present only in the coating material, while the core remains free of them. The experiments using coated chewing gums from the first batch shows that closure of the dentinal tubules can be achieved by formation of a dense layer of hydroxy apatite. Also in the second batch the formation of a smooth and mechanically stable layer that closes the dentinal tubules in a homogeneous fashion could be observed.

Sensory Properties

The agglomerate-containing hard-caramels, tablets and coated chewing gums displayed superior sensory properties. By visual inspection, only homogeneous areas of the apatite-gelatine-composite material can be detected. The surface of the products feel very smooth.

Example 7

SEM Comparative Test

For comparative purposes, scanning electron microscope (SEM) photos have also been made from hard caramel masses, wherein the apatite-gelatine-composite material has been used in the recipe of the hard caramel mass without first being agglomerated with at least one sugar alcohol in contrast to hard caramel masses made from agglomerates of the present invention.

Figure 9:
FIG. 9 shows the surface of an extruded hard caramel mass as a comparative example.

FIG. 9 shows apatite-gelatine-particles (clusters) on a partly-dissolved hard-caramel mass comprising the apatite-gelatine-composite material in pure form and not in form of the present agglomerates. The particles of the apatite-gelatine on the surface of the hard caramel mass cause roughness and an unpleasant sensoric feeling. They can even be observed visually.

Figure 10:
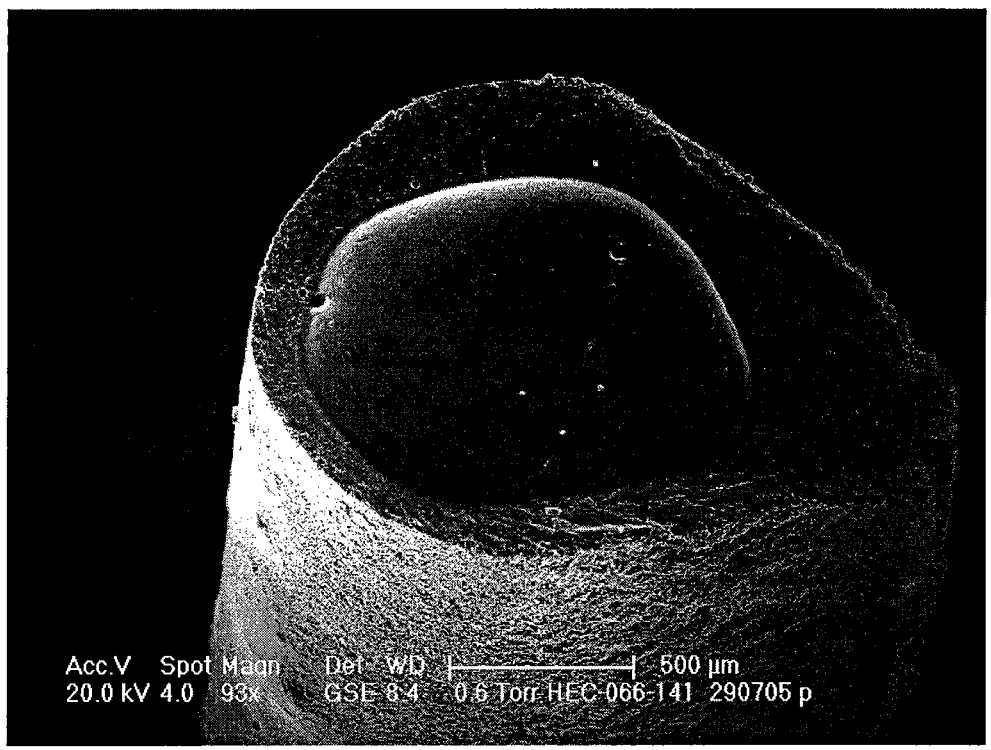
FIG. 10 shows the surface of an extruded hard caramel mass prepared with agglomerates of the present invention.

FIG. 10 shows a partly dissolved hard-caramel mass comprising the inventive agglomerates. The apatite-gelatine-composite material is homogenously distributed. No clustered apatite-gelatine particles can be observed, neither optically nor by SEM.

Thus, it can clearly be seen that the use of the agglomerates of the present invention comprising the at least one sugar alcohol in agglomerated form together with the apatite-gelatine-composite material drastically improves the distribution, in particular leads to a homogenous and finely divided distribution of the calcium component in the product and leads to improved products.

What is claimed is:

1. An agglomerate comprising a calcium-hydrocolloid-composite material and at least one sugar-alcohol, wherein the calcium-hydrocolloid-composite material comprises a calcium salt and a hydrocolloid component, wherein the agglomerate comprises 0.05 to 5.0 weight-% of the calcium hydrocolloid composite material, based on the dry weight of the agglomerate, and the agglomerate is prepared by a process comprising:
    a) providing the calcium-hydrocolloid-composite material and the at least one sugar alcohol; and
    b) distributing the calcium-hydrocolloid-composite material and the at least one sugar alcohol in a fluidizing bed under conditions suitable to agglomerate them, wherein the at least one sugar alcohol is in the form of particles, and wherein, in a first phase of step b) the at least one sugar alcohol is distributed in a fluidizing bed and, in a second phase, the calcium hydrocolloid-composite material is sprayed under pressure into the fluidized bed, and wherein agglomerate particles produced by the process steps a) and b) above exhibit a homogeneous distribution of the at least one sugar alcohol, the calcium salt and the hydrocolloid component throughout said particles and wherein said particles have a diameter of from 63 to 1000 µm.

2. The agglomerate according to claim 1, wherein 90% of said sugar alcohol particles have a diameter of less than 100 µm.

3. The agglomerate according to claim 1, wherein the agglomerate comprises the calcium salt in the form of particles having a diameter less than 1000 nm.

4. The agglomerate according to claim 3, wherein the particles of the calcium salt have a diameter of 5 to 300 nm.

5. The agglomerate according to claim 4, wherein the particles of the calcium salt have a diameter of 20 to 30 nm.

6. The agglomerate according to claim 1, wherein the calcium salt is selected from the group consisting of apatite, hydroxyapatite, fluoroapatite, fluorine-doped hydroxyapatite, carbonate-containing nonstoichiometric apatite, carbonate apatite and carbonated fluoroapatite.

7. The agglomerate according to claim 1, wherein the hydrocolloid is a protein component.

8. The agglomerate according to claim 1, wherein the hydrocolloid is selected from the group consisting of gelatine, gelatine hydrolysates, casein and casein hydrolysates.

9. The agglomerate according to claim 1, wherein the sugar-alcohol is selected from the group consisting of isomalt, isomalt GS, 1,1-GPM (1-O-α-D-glucopyranosyl-D-mannitol), 1,6-GPS (6-O-α-D-glucopyranosyl-D-sorbitol), 1,1-GPS (1-O-α-D-glucopyranosyl-D-sorbitol), a mixture of 1,1-GPS, 1,1-GPM and 1,6-GPS, xylitol, lactitol, mannitol, maltitol syrup, maltitol, sorbitol and erythritol.

10. The agglomerate according to claim 1, wherein the calcium salt is homogeneously distributed in the agglomerate.

11. The agglomerate according to claim 1, wherein at least one of the calcium salt and the calcium-hydrocolloid-composite material is coated by one or more surface modification agents.

12. The agglomerate according to claim 1, wherein the agglomerate has a diameter of 100 to 800 µm.

13. The agglomerate according to claim 1, wherein the agglomerate has a diameter of 100 to 500 µm.

14. The agglomerate according to claim 2, wherein the sugar-alcohol particles are distributed homogeneously in the agglomerate.

15. The agglomerate according to claim 1, wherein the calcium-hydrocolloid composite material and the at least one sugar-alcohol form at least 90% of the agglomerate, based on the dry weight of the agglomerate.

16. The agglomerate according to claim 1, wherein 95 to 99.95 weight-% of the agglomerate, based on dry weight of the agglomerate, is the at least one sugar-alcohol.

17. The agglomerate according to claim 1, wherein the calcium salt is a slightly water-soluble calcium salt.

18. The agglomerate according to claim 1, wherein the agglomerate further comprises at least one agglomerate additive.

19. The agglomerate according to claim 18, wherein the agglomerate additive is amorphous calcium phosphate and wherein said amorphous calcium phosphate is contained in the calcium-hydrocolloid-composite material.

20. A confectionery product, which comprises the agglomerate according to claim 1.

21. A confectionery product according to claim 20, which contains a product additive selected from the group consisting of intense sweeteners, gum bases, plastifiers, emulsifier, lubricant, protein components, milk components, fat and fat substitutes, vegetable fat, vitamins, minerals, pharmaceutically active ingredients, preservatives, aroma, flavourings, colours, $TiO_2$, edible acids and dietary fibres.

22. A confectionery product according to claim 20, which contains an intense sweetener selected from the group consisting of cyclamate, saccharin, aspartame, glycyrrhicine, neohesperidine-dihydrochalcone, steveoside, thaumatin, monellin, acesulfame, alitame, sucralose and mixtures thereof.

23. A confectionery product according to claim 20, which contains a product additive selected from the group consisting of a) casein phosphopeptide-amorphous calcium phosphate (CPP-ACP), b) tetracalciumphosphate/dicalciumphosphate, c) a two-phase system comprising a water soluble calcium compound and a water soluble inorganic phosphate in combination with at least one soluble fluorine compound, d) potassium salt, e) strontium salt, f) a combination of strontium and zinc ions, g) a modified enzyme comprising an enzyme and a polyanionic domain, h) bioactive glass particles, I) a complex or arginine, calcium, carbonate and dicarbonate, and j) combinations thereof.

24. A confectionery product according to claim 20, wherein the confectionery product is selected from the group consisting of chewing gums, jelly, gum, tablets, nougat, fudge, fondant, toffee, pastille, lozenge, a chocolate product, hard candies and soft candies.

25. A confectionery product according to claim 20, wherein the confectionery product is a coated product.

26. A confectionery product, wherein at least 90% of the confectionery product or of a coating of the confectionery product is comprised of an agglomerate according to claim 1, based on dry weight.

27. A confectionery product according to claim 20, wherein the agglomerate is contained in a coating of said product.

28. A hard candy according to claim 20, wherein the agglomerate comprises isomalt or isomalt GS as the at least one sugar alcohol.

29. A coated product selected from the group consisting of coated chewing gum, coated soft candy and a coated tablet according to claim 20, wherein the agglomerate comprises isomalt or isomalt GS as the at least one sugar alcohol.

30. A process for the preparation of an agglomerate comprising a calcium-hydrocolloid-composite material and at least one sugar-alcohol, wherein the process comprises:
 a) providing a calcium-hydrocolloid-composite material and at least one sugar-alcohol;
 b) distributing the calcium-hydrocolloid-composite material and the at least one sugar-alcohol in a fluidizing bed under conditions suitable to agglomerate them, wherein the at least one sugar alcohol is in the form of particles; and
 c) subjecting the agglomerate of step b) to size fractionation,
wherein agglomerate particles produced by the process steps a) to c) above exhibit a homogeneous distribution of the at least one sugar alcohol, the calcium salt and the hydrocolloid component throughout said particles and wherein said particles have a diameter of from 63 to 1000 μm.

31. The process according to claim 30, wherein the fluidizing bed is a stream of gas or liquid.

32. The process according to claim 31, wherein the fluidizing bed is an air stream.

33. The process according to claim 30, wherein the at least one sugar-alcohol is provided in solid form.

34. The process according to claim 30, wherein the calcium-hydrocolloid-composite material is provided as an aqueous dispersion.

35. The process according to claim 32, wherein the calcium-hydrocolloid material is sprayed under pressure into the fluidizing air stream.

36. The process according to claim 30, wherein the calcium-hydrocolloid-composite material has a temperature from 30 to 80° C.

37. The process according to claim 32, wherein the at least one sugar alcohol is sprayed under pressure into the fluidizing air stream.

38. The process according to claim 30, wherein the first phase of step b) the at least one sugar alcohol is distributed in the fluidizing bed and in the second phase the calcium-hydrocolloid-composite material is distributed therein.

39. The process according to claim 30, wherein the agglomeration in step b) is performed in a fluidizing bed agglomerator.

40. The process according to claim 30, wherein the agglomerate obtained in step b) is dried after agglomeration.

41. The process according to claim 30, wherein the agglomerate is dried after size-fractionation.

42. An agglomerate, obtained by the process of claim 30.

43. A method for therapeutically treating pain-sensitive teeth in an animal or human being in need thereof, comprising administering an effective amount of the agglomerate according to claim 1 or the confectionery product according to claim 20.

44. A method for therapeutically treating caries in an animal or human being in need thereof, comprising administering an effective amount of the agglomerate according to claim 1 or the confectionery product according to claim 20.

45. A method for the therapeutically remineralizing tooth defects in an animal or human being in need thereof, comprising administering an effective amount of the agglomerate according to claim 1 or the confectionery product according to claim 20.

46. The agglomerate according to claim 2, wherein 90% of said particles have a diameter of less than 50 μm.

47. The agglomerate according to claim 17, wherein the slightly water-soluble calcium salt is in the form of rod-shaped crystals.

48. The process according to claim 36, wherein the calcium-hydrochloride composite material has a temperature from 55 to 60° C.

49. The agglomerate according to claim 1, wherein the agglomerate has a uniform and microscopically homogeneous three-dimensional distribution of the calcium-hydrocolloid-composite material throughout the entire agglomerate.

* * * * *